United States Patent [19]

Takeuchi et al.

[11] 4,180,913

[45] Jan. 1, 1980

[54] α-CYANOACRYLATE DENTAL MATERIAL AND METHOD OF PREPARATION

[75] Inventors: Mitsuharu Takeuchi, No. 2-16-19, Ichikawa, Ichikawa-shi, Chiba-ken, Japan; Satoshi Hayashi, Odawara; Isao Minemoto, Matsudo, both of Japan

[73] Assignees: Lion Hamigaki Kabushiki Kaisha; Mitsuharu Takeuchi, both of Tokyo, Japan

[21] Appl. No.: 851,080

[22] Filed: Nov. 14, 1977

[30] Foreign Application Priority Data

Nov. 13, 1976 [JP] Japan ................................ 51/136782
Nov. 13, 1976 [JP] Japan ................................ 51/136783

[51] Int. Cl.$^2$ .............................................. C08K 9/04
[52] U.S. Cl. ................................ 433/228; 260/42.16; 260/998.11; 428/404
[58] Field of Search ............. 32/15; 260/42.16, 998.11

[56] References Cited

U.S. PATENT DOCUMENTS

| | | | |
|---|---|---|---|
| 3,663,501 | 5/1972 | Adams ................................ | 260/42.16 |
| 3,940,362 | 2/1976 | Overhults ........................... | 260/42.16 |
| 3,986,261 | 10/1976 | Faunce ................................ | 32/15 X |
| 4,012,840 | 3/1977 | Takeuchi et al. ................... | 32/15 |

*Primary Examiner*—Sandra M. Person
*Attorney, Agent, or Firm*—Blum, Kaplan, Friedman, Silberman & Beran

[57] ABSTRACT

A filler for an α-cyanoacrylate dental material comprising a silica powder coated with at least one solid catalyst having a weak catalytic activity to the α-cyanoacrylate. Solid catalysts include amino acids and acidamide compounds. The dental material is prepared by mixing an α-cyanoacrylate with the filler. The mixture is applied to the tooth and a setter composition comprising a basic amine compound having a strong catalytic activity to the α-cyanoacrylate is applied to cure the dental material.

22 Claims, No Drawings

α-CYANOACRYLATE DENTAL MATERIAL AND METHOD OF PREPARATION

BACKGROUND OF THE INVENTION

This invention relates generally to a dental material comprising as a main ingredient an α-cyanoacrylate and in particular to a filler for a pit and fissure sealant, an adhesive pit and fissure sealant comprising this filler, and a method for preparing the filler and the adhesive pit and fissure sealant.

In dental practice, known sealing and adhesive compositions include α-cyanoacrylate type compositions, methyl methacrylate type compositions and bis-GMA type compositions. However, each of these compositions possess defects in their application. For example, for the methyl methacrylate type and the bis-GMA type compositions where a catalyst and a monomer are mixed on application, curing is completed in 2 to 5 minutes. The teeth must be coated very promptly and the mouth must remain open after coating until curing is completed. Coating of compositions cured by radiation with ultraviolet rays can be facilitated since the working time is long. However, ultra-violet rays must be applied for more than 1 minute after coating until curing is completed and the mouth must be opened during this period. Accordingly, patients may undergo much pain. On the other hand, for α-cyanoacrylate type compositions the curing time is short because of a high anionic polymerizing property. However, they are cured readily by water in the air or water adhering to teeth, and therefore, control is very difficult and application is often impossible.

As a means for overcoming these defects, Japanese Patent Application Laid-Open Specification No. 119984/74 (corresponding to U.S. Pat. No. 4,012,840) proposes a method in which dimethyl formamide is added to a mixture of an α-cyanoacrylate and a filler. The resulting composition is applied and a setter is dropped thereon to effect curing. Various advantages are attained according to this method. For example, the working time is prolonged, polymerization shrinkage is reduced by preliminary polymerization, application is facilitated, and curing is accomplished promply by dropping a setter after the application. However, the above-mentioned mixture of an α-cyanoacrylate and a filler is very unstable and it is readily thickened and solidified within a relatively short period. The filler is precipitated readily and guarantee or maintenance of the quality of the product is difficult. More specifically, if a catalyst and a filler are added independently to an α-cyanoacrylate, a suitable thixotropic property cannot be obtained. Further, if DMF (N,N-Dimethyl formamide) is dropped thereon as a preliminary polymerization agent at the time of application, the majority of the composition is solidified to form so called "particulated polymer". The term "particulated polymer" used in the specification refers to a partially polymerized mass which precipitates immediately after addition of catalyst. When particulated polymer forms, the amount of resulting composition that can be used is reduced to ¼ of the original amount, resulting in a great loss of the composition. Moreover, it is very difficult to drop a prescribed amount of dimethyl formamide as a catalyst. For example, when the composition is used as a caries-preventing agent, the amount of composition used for one application is ordinarily about 100 mg. and a suitable amount of dimethyl formamide is 2 to 10 mg. This latter amount corresponds to 1 to 5 drops when dimethyl formamide is dropped by using a micro syringe. It is likely that the dimethyl formamide will be added excessively unless addition is carried out very carefully. If dimethyl formamide is added in excess, the bonding strength is reduced. Therefore, handling of the composition of this type involves various difficulties. In the preparation process, in order to prevent increase of the viscosity or solidification, an α-cyanoacrylate stabilizer, such as $SO_2$ or an acid is added. In this case, the stability is improved, but properties of the composition as a polymeric material are degraded, and pelling, cracking and leakage readily occur in the resulting coating in the applied oral cavity and the practical utility of the composition is lost. Still further, when a composition is prepared by dispersing a filler in an α-cyanoacrylate, it is necessary to heat the filler at 600° to 700° C. for about 2 hours in order to remove water from the filler which acts as a catalyst. Even in the so heat-treated filler is dispersed in the α-cyanoacrylate polymerization advances within about 3 to about 6 months and an increase in viscosity is observed.

When a thixotropic composition is prepared by adding a catalyst to a mixture of an α-cyanoacrylate and a filler, it is difficult to prepare the intended thixotropic composition in a short time as a solid catalyst disperses poorly in the α-cyanoacrylate. Further, when a liquid catalyst other than dimethyl formamide is used, it is difficult to obtain a suitable thixotropic composition. A liquid catalyst having an activity similar to that of dimethyl formamide has not been found.

Japanese Patent Publication No. 47290/72 proposes use of a mixture of an α-cyanoacrylate, and organic solid powdery substance and an alkaline polymerization catalyst. As will be apparent from Table I set forth below, this proposal is not satisfactory in that the dispersibility is poor and a satisfactory thixotropic composition is not obtained. More specifically, since the particle size of the solid powdery substance is coarse, particulated polymer is formed readily and a good thixotropic composition is not obtained and the composition cannot be coated on surfaces of teeth. The curing property of the composition is determined substantially by the kind and amount of alkaline polymerization catalyst used and the working time is very short so that when the composition is cured instantly handling becomes difficult.

Japanese Patent Application Laid-Open Specification No. 12125/75 discloses an adhesive comprising an α-cyanoacrylate and a powder coating with a basic amine catalyst. The amine catalyst used in this adhesive has a very high catalytic activity, and if this amine catalyst is coated on an ultra-microfine silica, reaction takes place locally. Heat is generated instantly causing curing when the coated silica is mixed with the α-cyanoacrylate. Further, particulated polymer is formed readily and a good thixotropic composition is not obtained. Moreover, according to this proposal, the preliminary treatment must be conducted with a silane coupling agent in order to prevent reduction of catalytic activity.

In a cyanoacrylate type composition disclosed in Japanese Patent Application Laid-Open Specification No. 128790/75 porous particles having a coarse particle size and containing an amine catalyst are disclosed. As the amine catalyst used has a very high activity and the time required for curing is determined substantially by the kind and amount of the catalyst and the surface condition of the carrier particles, particulated polymer is formed readily and a homogeneous thixotropic composition is not obtained. Therefore, a material that can be applied effectively for attaining special effects required in the dental use is not obtained. Moreover, various problems mentioned above with respect to Japanese Patent Application Laid-Open Specification No. 119984/74 similarly are encountered in production of compositions of this type.

Accordingly, it would be desirable to provide a filler for an α-cyanoacrylate dental material when mixed with the α-cyanoacrylate yields a thixotropic dental material of sufficient working time which can be cured instantly.

SUMMARY OF THE INVENTION

Generally speaking, in accordance with the invention, a filler for a dental material containing an α-cyanoacrylate is provided which comprises a silica powder coated with at least one solid catalyst having a weak catalytic activity to the cyanoacrylate. The solid catalyst is at least one member selected from the group consisting of amino acids and acid-amide compounds and is coated on the silica powder to form the filler. The filler is mixed with the α-cyanoacrylate to form a thixotropic dental material which may be used to seal pits and fissures of teeth. A setter comprising a basic amine compound having a strong catalytic activity to the α-cyanoacrylate is added to the applied dental material to cure the α-cyanoacrylate instantly.

Accordingly, it is an object of the invention to provide an improved filler for a dental material including an α-cyanoacrylate.

Another object of the invention is to provide an improved filler for a dental material containing an α-cyanoacrylate capable of forming, together with the α-cyanoacrylate, a good thixotropic composition that can be instantly cured by polymerization reaction with a setter.

A further object of the invention is to provide an improved thixotropic dental material comprising an α-cyanoacrylate which can be cured instantly.

Still another object of the invention is to provide an improved adhesive pit and fissure sealant which can be formed into a thixotropic composition, has a very long working time and has such a curing property that it can be cured optionally at any time within several seconds to scores of seconds.

Another object of the invention is to provide a method for preparing the filler and the dental material containing an α-cyanoacrylate.

Yet another object of the invention is to provide a method for applying the improved filler and dental material containing an α-cyanoacrylate to a patient's teeth.

Still other objects and advantages of the invention will in part be obvious and will in part be apparent from the specification.

The invention accordingly, comprises the several steps and the relation of one or more of such steps with respect to each of the others, and the composition possessing the features, properties, and the relation of constituents, which are exemplified in the following detailed disclosure, and the scope of the invention will be indicated in the claims.

DESCRIPTION OF THE PREFERRED EMBODIMENTS

In accordance with one embodiment of the present invention, a filler for a dental material containing an α-cyanoacrylate is provided. The filler is capable of forming, together with the α-cyanoacrylate, a thixotropic composition that can be cured instantly by polymerization reaction with a setter. The filler comprises a silica powder substrate coated with at least one solid catalyst selected from the group consisting of amino acids and acid-amide compounds having a weak catalytic activity to the α-cyanoacrylate.

In accordance with another embodiment of the present invention, there is provided a dental material formed by mixing an α-cyanoacrylate and a filler comprising a silica powder substrate coated with at least one solid catalyst selected from the group consisting of amino acids and acid-amide compounds having a weak catalytic activity to the α-cyanoacrylate. The dental material is cured by adding a basic amine compound having a strong catalytic activity to the α-cyanoacrylate. The basic amine compounds are those having a pKb value of 1 to 12 in water.

The α-cyanoacrylate used in the present invention is at least one member selected from the group consisting of compounds represented by the following general formula:

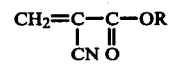

wherein R stands for an alkyl group having from 1 to 16 carbon atoms, a cyclohexyl group, a phenyl group or the like.

Compounds represented by the above formula are, for example, ethyl α-cyanoacrylate, methyl α-cyanoacrylate, butyl α-cyanoacrylate, isobutyl α-cyanoacrylate, amyl α-cyanoacrylate and lauryl α-cyanoacrylate. Ethyl α-cyanoacrylate is preferred.

The fillers of the present invention capable of forming a good thixotropic composition together with the α-cyanoacrylate comprise a silica powder as a substrate. The silica powder is coated with at least one solid catalyst selected from the group consisting of amino acids and acid-amide compounds having a weak catalytic activity to the α-cyanoacrylate.

The silica powder used as the substrate may be an inorganic powder composed of silica substantially free of impurities, an inorganic powder composed of silica containing a small amount of alumina and an inorganic powder composed of silica containing a small amount of titanium oxide. Each powder used is in the form of ultra-microfine particles having a size not larger than 100 mμ, preferably a particle size in the range of from 1 to 100 mμ. When the particle size is larger than 100 mμ, the powder is readily precipitated and phase separation takes place, and a good thixotropic property is not attained. Accordingly, use of a powder having a size larger than 100 mμ should be avoided. The reason why such powder composed mainly of silica is used as a filler substrate in the present invention is that the dispersibility and thixotropic property are influenced by a filler substrate as shown in Table I:

Table I
CHARACTERISTICS OF FILLER SUBSTRATES

| Coating Agent | Filler Substrate | Amount of Filler | | | | Remarks |
|---|---|---|---|---|---|---|
| | | 10 parts by weight | | 20 parts by weight | | |
| | | dispersibility | thixotropic property | dispersibility | thixotropic property | |
| In each case 10 parts by weight of acetamide per 100 parts by weight of substrate | Aerosil OX-50 | O | O | O | O | 1—100 m$\mu$ (Average Size 50 m$\mu$) 100% SiO$_2$ 90% SiO$_2$ |
| | *celite | X | X | X | X | 1.6–3.8 $\mu$ |
| | alumina hydrate | ▲ | X | ▲ | X | below 10 $\mu$, 60–80% Al$_2$O$_3$ |
| | active alumina | ▲ | X | ▲ | X | below 10 $\mu$, 70–90% Al$_2$O$_3$ |
| | apatite | X | X | X | X | below 20 $\mu$ |
| | **chunipia | X | X | X | X | silica-alumina mixture |
| | bentonite | O | X | O | X | below 20 $\mu$ |
| | polymethyl methacrylate | O | X | O | X | 300–325 mesh (about 40 $\mu$) |
| | carboxymethyl cellulose | X | X | X | X | 50–100 $\mu$ |

NOTE:
*Wako Junyaku Kabushiki Kaisha: Trademark
**Kunimine Koka Kogyo Kabushiki Kaisha: Trademark In Table I to IV, "Amount of Filler" means an amount (parts by weight) of the solid catalyst-coated filler (some comparative fillers are not coated in Table IV) per 100 parts by weight of the α-cyanoacrylate.

The symbols used in the Tables I to IV have the following meaning:

(A) Evaluation of Thixotropic Property:
O: the sample shows flowability when a light shock is given; good condition
Δ : the sample is slightly flowable even if a shock is not given; lowly thixotropic condition
▲ : the sample shows flowability only when a strong shock is given; excessively thixotropic condition
X: the sample shows flowability even if a shock is not give or the sample is solidified; no thixotropic property (B) Evaluation of Dispersibility:
O: seemingly uniformly dispersed
Δ : seemingly partially coagulated
X: seemingly substantially coagulated The "Aerosil" substrate used in Table I to IV is a trademark for a filler substrate composed of silica, and grades of respective filler substrates are as follows:

Aerosil MOX-170: surface area of 170 m$^2$/g as measured according to the BET method, 1% of alumina contained Aerosil 300: surface area of 300 m$^2$/g as measured according to the BET method, particle size of 1 to 30 m$\mu$ (average particle size of 7 m$\mu$)

Aerosil 200: surface area of 200 m$^2$/g as measured according to the BET method, particle size of 1 to 30 m$\mu$ (average particle size of 10 m$\mu$)

Aerosil OX-50: surface area of 50 m$^2$/g as measured according to the BET method, particle size of 1 to 100 m$\mu$ (average particle size of 50 m$\mu$)

Aerosil R-972: silica having hydrophobic characteristic

At least one solid catalyst selected from the group consisting of amino acids and acid-amide compounds having a weak activity to the α-cyanoacrylate is used for coating the filler substrate. As the amino acid, monoamino-monocarboxylic acids and monoamino-dicarboxylic acids may be used. Preferably, glycine, valine, methionine, glutamic acid and tyrosine are used singly or in combination as a coating material. As the acid-amide compound, acetamide, butyramide, α-chloroacetamide and benzamide may be used singly or in combination as the coating material. Of course, an amino acid and an acid-amide compound may be used in combination.

The silica substrate is coated with from about 1 to 50 parts by weight, preferably from about 5 to 30 parts by weight, of the amino acid and acid-amide solid catalysts per 100 parts by weight of the substrate. Examples of preparing the coated filler material are as follows.

EXAMPLE 1

A filler coated with an amino acid solid catalyst was preprared as follows:

(a) 1 g of a silica powder (having a particle size of 1 to 100 m$\mu$), (b) 0.05 g of glycine and (c) 30 ml of a solvent (water) were placed in a conical beaker, and the mixture was agitated for about 1 hour by a magnetic stirrer. Water was evaporated on a water bath and the residue was subjected to reduced pressure drying (for 5 hours). The resulting dry product was finely divided by a pulverizer resulting in a filler comprising the substrate coated with the solid catalyst in accordance with the present invention.

EXAMPLE 2

A filler coated with an acid-amide solid catalyst was prepared as follows:

(a) 1 g of a silica powder (having a particle size of 1 to 100 m$\mu$), (b) 0.2 g of acetamide and (c) 50 ml of a solvent (methanol) were placed in a conical beaker and the mixture was agitated for about 1 hour by a magnetic stirrer. Methanol was removed on a water bath and the residue was dried under reduced pressure. The resulting agglomerated filler was finely divided by a pulverizer resulting in a solid catalyst-coated filler in accordance with the invention.

In accordance with the invention, it is important that a filler substrate is coated with a solid catalyst having a weak activity, such as mentioned above. By virtue of this feature, coagulation or agglomeration of the filler particles can be prevented effectively and formation of particulated polymer by local solidification of the cyanoacrylate on the surfaces of the filler particles can be prevented, whereby the working time can be prolonged and the quality can be assured.

When a catalyst having a strong activity is used for coating, particulated polymer is formed by local solidification of the cyanoacrylate on the filler surface, and a thixotropic composition cannot be attained. When the above-mentioned liquid catalyst, such as dimethyl formamide is used for coating, agglomeration or cohesion of filler particles readily takes place, and the filler surface is kept wet and the dispersibility is reduced. Moreover, since the catalyst is evaporated during storage, the amount of the catalyst is reduced. Therefore, use of a solid catalyst having a weak activity, which is free of the foregoing defects, is important.

Various types, amounts and catalytic activities of amino acids as the solid catalyst are shown in Table II.

Various types, amounts and catalytic activities of acid-amide compounds as the solid catalyst are shown in Table III.

In Tables II and III, the Aerosil OX-50 (Trademark) was used as a filler substrate.

In Tables II to IV, "Coated Amount" means an amount coated (parts by weight) of the solid catalyst per 100 parts by weight of the filler substrate composed mainly of silica.

The setter compositions having a strong catalytic activity to the α-cyanoacrylate used in the present invention comprise basic amine compounds having a pKb value of 1 to 12. Preferred examples of such basic amine compounds are curing promotors, such as N,N-dimethyl-p-toluidine, N,N-diethyl-p-toluidine, N,N-dimethylaniline and N,N-diethylaniline. In general, the setter is used dissolved in a solvent, such as ethanol or n-hexane, preferably at a concentration of from about 0.1 to 5 weight/volume %. The preferred setters cure the thixotropic composition prepared by the present invention instantly, namely within a very short period of several seconds to scores of seconds, preferably within 5 seconds.

Table II

| | | Amount Coated | | | |
|---|---|---|---|---|---|
| Coating | | 10 parts by weight | | 5 parts by weight | |
| Compound (Catalyst) | Amount of Filler | dispersibility (B) | thixotropic property (A) | dispersibility (B) | thixotropic property (A) |
| glycine | 10 parts by weight | O | O | O | O |
| valine | " | O | O | O | O |
| methionine | " | O | O | O | O |
| glutamic acid | " | O | O | O | O |
| lysine | " | X | Δ | Δ | Δ |
| arginine | " | X | X | Δ | Δ |
| phenylalanine | " | O | O | O | Δ |
| tyrosine | " | O | O | O | O |
| Tryptophan | " | O | Δ | O | Δ |
| gamma-aminobutyric | " | X | X | O | Δ |
| epsilon-aminocaproic acid | " | X | X | Δ | O |

NOTES:
(A) Evaluation of Thixotropic Property:
O : good condition
Δ: lowly thixotropic
▲ : excessively thixotropic
X : no thixotropic property
(B) Evaluation of Dispersibility:
O : seemingly uniformly dispersed
Δ : seemingly partially coagulated
X : seemingly substantially coagulated Table III

| | | Amount of Filler (per 100 parts α-cyanoacrylate) | | | |
|---|---|---|---|---|---|
| Coating | | 10 parts by weight | | 15 parts by weight | |
| Compound (catalyst) | Amount Coated (parts by weight) | dispersibility (B) | thixotropic property (A) | dispersibility (B) | thixotropic property (A) |
| acetamide | 30 | O | O | O | O |
| " | 20 | O | O | O | O |
| " | 15 | O | O | O | O |
| " | 10 | O | O | O | O |
| " | 5 | O | O | O | O |
| butyramide | 30 | O | O | O | O |
| " | 10 | O | O | O | O |
| " | 1 | O | X | O | X |
| alpha-chloroacetamide | 30 | O | O | O | O |
| " | 10 | O | O | O | O |
| " | 1 | O | X | O | Δ |
| benzamide | 30 | O | O | O | O |
| " | 10 | O | O | O | O |
| benzanilide | 30 | O | X | X | O |
| " | 10 | O | X | O | X |
| thiourea | 10 | X | X | X | X |
| " | 3 | X | X | X | X |

Table III-continued

| | | CHARACTERISTICS OF ACID-AMIDE CATALYSTS | | | |
|---|---|---|---|---|---|
| | | Amount of Filler (per 100 parts α-cyanoacrylate) | | | |
| Coating | | 10 parts by weight | | 15 parts by weight | |
| Compound (catalyst) | Amount Coated (parts by weight) | dispersibility (B) | thixotropic property (A) | dispersibility (B) | thixotropic property (A) |
| " | 1 | X | X | X | X |
| 1,3-diphenyl urea | 30 | X | X | X | X |
| " | 10 | X | X | X | X |
| succinamide | 10 | X | X | X | X |
| phthalimide | 10 | X | X | X | X |
| nicontinamide | 10 | X | X | X | X |
| " | 1 | X | X | X | X |

NOTES:
(A)Evaluation of Thixotropic Property:
O : good condition
Δ : lowly thixotropic
▲ : excessively thixotropic
X : no thixotropic property
(B)Evaluation of Dispersibility:
O : seemingly uniformly dispersed
Δ : seemingly partially coagulated
X : seemingly substantially coagulated In accordance with the invention, since the filler to be mixed with the α-cyanoacrylate is in the form of ultra-microfine particles having a size not exceeding 100 mμ, the sealant including the filler intrudes sufficiently into fine pores in the tooth formed by an acid treatment of the enamel surfaces, whereby high mechanical bonding strength can be attained.

In general, thixotropic compositions formed according to the present invention can be used effectively within about 1 to about 2 hours after preparation. If the setter noted above is dropped onto this thixotropic composition, the composition can be cured substantially instantly. Accordingly, when the compositions are used as a dental material, patient discomfort is diminished markedly and the compositions have a high practical utility.

In accordance with the invention, the mixing ratio of the filler to α-cyanoacrylate varies depending on the kind of catalyst coated on the filler substrate. In general, as shown in Table IV below, when the filler is composed mainly of particles having a size of about 10 mμ, the filler is used in an amount from about 5 to 13 parts by weight, and preferably from about 7 to 10 parts by weight per 100 parts by weight of the α-cyanoacrylate.

When the filler has a broad particle size distribution range of 1 to 100 mμ, the filler is used in amounts of from about 5 to 25 parts by weight and preferably from about 8 to 18 parts by weight per 100 parts by weight of the α-cyanoacrylate. When such mixing ratios are adopted, good thixotropic compositions are obtained. If the amount of the filler is less than the above noted ranges, good thixotropic compositions are not obtained.

As shown in Table IV, a thixotropic composition may be obtained in certain cases even if a filler not coated with the solid catalyst of the invention is used. However, when a setter is applied, extreme heat is generated and the composition becomes brittle due to the fact that it is not preliminarily polymerized.

When applying the composition of the present invention as a dental caries preventing sealant a predetermined amount of a filler coated with a solid catalyst is mixed with a corresponding amount of an α-cyanoacrylate in a mixing machine such as an amalgam mixer. Occlusal surfaces of molars are treated for a certain time with a solution of an acid such as phosphoric acid. The surfaces are washed in running water and are dried with compressed air. The above thixotropic composition is applied thinly on the dired surfaces by means of a brush. A setter comprising a solution of, for example, N,N-dimethyl-p-toluidine is dropped onto the applied surfaces to cure the applied composition instantly.

Table IV

| | EVALUATION OF THIXOTROPIC PROPERTY | | | | | | | | | | | |
|---|---|---|---|---|---|---|---|---|---|---|---|---|
| | | Amount (parts by weight) of Filler (per 100 parts α-cyanoacrylate) | | | | | | | | | | |
| Coating Compound | Filler Substrate | 4 | 5 | 6 | 7 | 8 | 10 | 12 | 13 | 20 | 22 | 25 | 30 |
| 10 parts by weight of acetamide per | Aerosil MOX-170 | | X | O | O | O | O | O | ▲ | | | | |
| 100 parts by weight of substrate | Aerosil 300 | X | Δ | O | O | O | O | O | ▲ | X | | | |
| | Aerosil 200 | X | Δ | O | O | O | O | O | ▲ | X | | | |
| | Aerosil OX-50 | X | Δ | O | O | O | O | O | O | O | O | ▲ | X |
| | Aerosil R-972 | | | | | X | | | | | | | |
| not coated | Aerosil MOX-170 | | Δ | O | O | ▲ | X | | | | | | |
| | Aerosil 300 | Δ | O | O | ▲ | | | | | | | | |
| | Aerosil OX-50 | | | | | | | | | X | X | O | O |

NOTES:
Evaluation of Thixotropic Property:
O : good condition
Δ : lowly thixotropic
▲ : excessively thixotropic
X : no thixotropic When compositions of the present invention are used as an agent for preventing advance of early caries, they can be applied in the same procedures as described above without forming a cavity in a carious tooth. When the composition of the present invention is used as an adhesive material for orthodontics, it is not applied to the occlusal surfaces of molar but to smooth surfaces of incisor and premolar. A bracket is placed on the applied surfaces and the catalyst solution is dropped thereon. Of course, the composition of the present invention can be used not only for the dental application but also for an ordinary adhesive material conveniently.

The present invention will now be described in detail by reference to the following Examples.

EXAMPLE 3

First component: ethyl α-cyanoacrylate (sold under trademark "Aron Alpha D Sankyo": Toa Gosei Kagaku Kogyo K.K.)

Second component: filler (formed by coating 100 parts by weight of silica powder having a broad particle size distribution range of 1 to 100 mµ with 10 parts by weight of acetamide)

Third component: setter composed of a 2% solution of N,N-dimethyl-p-toluidine in ethanol To 100 parts by weight of the first component was added 10 parts by weight of the second component, and the mixture was blended to form a thixotropic composition. The occlusal surfaces of molar were treated with a phosphoric acid solution having a concentration of 3 moles per liter for 1 minute, followed by washing in running water and drying. The above thixotropic composition was thinly applied on the surfaces and penetrated into pits and fissures. Then, one drop of the third component, i.e., the setter, was applied to the applied tooth surfaces to effect curing. Thus, the application was completed.

EXAMPLE 4

First component: ethyl α-cyanoacrylate

Second component: filler (formed by coating 100 parts by weight of silica powder containing 1% of alumina and having a particle size of 1 to 30 mµ with 10 parts by weight of glycine)

Third component: setter composed of a 2% solution of N,N-dimethyl-p-toluidine in hexane To 100 parts by weight of the first component was added 10 parts by weight of the second component, and the mixture was blended to form a thixotropic composition. The occlusal surface of molar were treated with a phosphoric acid solution having a concentration of 5 moles per liter for 30 seconds, and the above thixotropic composition was applied thinly on the treated tooth surfaces and penetrated into pits and fissures. Then, 1 to 2 drops of the third component, i.e., the setter, was applied to the tooth surfaces to effect curing. Thus, the application was completed.

EXAMPLE 5

First component: isobutyl α-cyanoacrylate

Second component: filler (formed by coating 100 parts by weight of silica powder having a particle size of 1 to 30 mµ with 30 parts by weight of butyramide)

Third component: setter composed of a 0.5% solution of N,N-diethyl-p-toluidine in ethanol To 100 parts by weight of the first component was added 10 parts by weight of the second component, and the mixture was blended to form a thixotropic composition. The occlusal surfaces of molar of a patient were polished and treated with a 20% aqueous solution of citric acid for 1 minute, followed by washing in running water and drying. The above thixotropic composition was thinly applied on the treated tooth surfaces over entire crown portions and penetrated into pits and fissures. Then, the third component, i.e., the setter, was dropped to the applied tooth surfaces. Thus, the application was completed.

EXAMPLE 6

First component: methyl α-cyanoacrylate

Second component: filler (formed by coating 100 parts by weight of silica powder having a particle size of 1 to 30 mµ with 20 parts by weight of alpha-chloracetamide)

Third component: setter composed of a 5% solution of N,N-dimethyl-p-toluidine in ethanol To 100 parts by weight of the first component was added 12 parts by weight of the second component and the mixture was blended to form a thixotropic composition. The occlusal surfaces of molar were treated with a phosphoric acid solution having acconcentration of 3 moles per liter for 30 seconds. The above thixotropic composition was thinly applied on the treated tooth surface and sufficiently penetrated into pits and fissures. Then, 1 to 2 drops of the third component, i.e., the setter, was applied to the tooth surfaces to effect curing. Thus, the application was completed.

In each of the foregoing Examples, if a predetermined amount of the second component was placed in a capsule and mixed with a corresponding amount of the first component by means of a mixing machine, such as an amalgam mixer, a more homogeneous thixotropic composition can be obtained in a short time.

Accordingly, in accordance with the invention, a dental composition is obtained which is characterized by a thixotropic property so that it can be applied easily by a brush or the like, provides high mechanical bonding strength. These characteristic properties of the compositions of the present invention have been confirmed by the following experiments.

Experiment I (Thixotropic Property)

The composition prepared in accordance with the above-mentioned Japanese Patent Application Laid-Open Specification No. 19984 (U.S. Pat. No. 4,012,840) formed by adding dimethyl formamide as a second component to a first component comprising an α-cyanoacrylate and silica results in particulated polymer formed. In contrast, when an α-cyanoacrylate is mixed with a silica powder coated with the catalyst at the time of the application according to the present invention, particulated polymer is not formed at all, but a homogeneous thixotropic composition is obtained. In other words, the present invention prevents formation of particulated polymer and the entire composition is rendered thixotropic.

Experiment II (Stability of Composition)

(A) Samples:

Sample A: ethyl α-cyanoacrylate (sold under trademark "Aron Alpha D Sankyo": Toa Gosei Kagaku Kogyo K.K.)

Sample B: composition disclosed in Japanese Patent Application Laid-Open Specification No. 119984/74 (U.S. Pat. No. 4,012,840), which comprises an α-cyanoacrylate and silica Sample C: composition formed by adding a stabilizer at a high concentration to the above sample B (the amount of the stabilizer is 2.5 times the amount of the Sample B)

Sample D: preserving vessel of the sample B is packaged with aluminum foil

Sample E: preserving vessel of the sample C is packaged with aluminum foil (B) Storage Conditions:

In a polyethylene vessel having a capacity of about 2 g, the sample is filled, and the sample is stored at a temperature of 50° C. and a relative humidity of 100% for 10 days.

(C) Results:

|  | Increase of Viscosity | Deformation of Vessel | Precipitation of Silica |
|---|---|---|---|
| Sample A | not changed | not changed | — |
| Sample B | extreme increase of viscosity | extreme deformation | observed |
| Sample C | observed | observed | observed |
| Sample D | observed | observed | not observed |
| Sample E | slight increase | slightly deformed | not observed |

Experiment III (Bonding Strength)

(A) Samples:

Sample A: composition according to the present invention (Examples 5–8)

Sample B: composition prepared from an α-cyanoacrylate and silica according to the disclosure of Japanese Patent Application Laid-Open Specification No. 119984/74 (U.S. Pat. No. 4,012,840)

Sample C: composition formed by adding to the sample B a stabilizer in an amount 2.5 times the amount of the sample B Sample D: commercially available product (B) Test Method:

The labial surface of an extracted bovine incisor was flattened by means of polishing and the surface is etched with an acid, washed with water and dried. A rod (having a diameter of 6 mm) of polymethyl methacrylate was bonded to the so treated enamel surface by using the samples. The bonded tooth was allowed to stand still overnight in water maintained at 37° C., and the tensile strength was measured by a tensile tester and the bonding strength per unit area was determined.

(C) Results:

|  | Bonding Strength (Kg/cm$^2$) | Standard Deviation |
|---|---|---|
| Sample A | 174.2 | 39.6 |
| Sample B | 166.7 | 38.2 |
| Sample C | 93.1 | 21.9 |
| Sample D | 79.3 | 28.7 |

Accordingly, in accordance with the present invention, when an α-cyanoacrylate is mixed with a predetermined amount of a filler coated with a prescribed amount of a solid catalyst having a weak activity to the α-cyanoacrylate particulated polymer is not formed, and a composition which is entirely thixotropic is easily obtained. The filler is maintained separately from the α-cyanoacrylate and they are mixed together at the time of application. Therefore, the handling is facilitated remarkably. A variety of catalysts can be used and the application range of the material can be broadened. Still in addition, the working time of the thixotropic composition prepared in accordance with the invention is as long as 1 to 2 hours, and if a solution of a strong catalyst (setter) is dropped after its application, the composition is instantly cured. Therefore, a patient may close his mouth promptly and undergoes no pain. Still further, since the composition is thixotropic, it can be applied easily on the pits and fissures of a tooth in a uniform thickness, and since the polymerization is carried out in two stages, polymerization shrinkage is diminished and the influence of the inner stress is reduced. Accordingly, peeling or leakage of the composition is reduced markedly. Moreover, the composition of the present invention has an advantage that the bonding strength is very high.

The composition of the present invention which has a long working time and can be instantly cured at any optional time is very suitable as a dental material, especially as an adhesive pit and fissure sealant.

The compositions of the instant invention can also be used effectively as an instantaneous adhesive. The compositions are advantageous in that gelation is not caused even if it is stored for a long time, the quality is not changed even with the lapse of time and it has a very excellent storability.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A filler for an α-cyanoacrylate dental material comprising a silica powder substrate having a particle size range of from about 1 to 100 millimicrons coated with at least one solid catalyst having a weak catalytic activity to said α-cyanoacrylate, said solid catalyst being at least one member selected from the group consisting of amino acids and acid-amide compounds, said filler capable of forming a thixotropic composition with said α-cyanoacrylate, and said thixotropic composition capable of being cured by polymerization reaction with a setter.

2. The filler of claim 1, wherein said amino acid is at least one member selected from the group consisting of monoamino-monocarboxylic acids and monoamino-dicarboxylic acids.

3. The filler of claim 2, wherein said amino acid is at least one member selected from the group consisting of glycine, valine, methionine, glutamic acid and tyrosine.

4. The filler of claim 3, wherein from 1 to 50 parts by weight of said solid catalyst is coated on 100 parts by weight of said substrate.

5. The filler of claim 1, wherein said acid-amide compound is at least one member selected from the group consisting of acetamide, butyramide, α-chloroacetamide and benzamide.

6. The filler of claim 5 wherein from 1 to 50 parts by weight of said solid catalyst is coated on 100 parts by weight of said substrate.

7. A dental material formed by mixing an α-cyanoacrylate and a filler comprising a silica powder substrate having a particle size range of from about 1 to 100 mµ coated with at least one solid catalyst having a weak catalytic activity to said α-cyanoacrylate, said solid catalyst being at least one member selected from the group consisting of amino acids and acid-amide compounds to obtain a thixotropic composition whereby said material may be cured with a basic amine compound having a strong catalytic activity to said α-cyanoacrylate and a pKb value of 1 to 12 in water.

8. The material of claim 7, wherein said α-cyanoacrylate is at least one member selected from the group consisting of compounds represented by the general formula

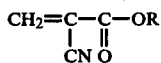

wherein R is an alkyl group having from 1 to 16 carbon atoms, a cyclohexyl group or a phenyl group.

9. The material of claim 8, wherein said α-cyanoacrylate is at least one member selected from the group consisting of ethyl α-cyanoacrylate, methyl α-cyanoacrylate, butyl α-cyanoacrylate, isobutyl α-cyanoacrylate, amyl α-cyanoacrylate and lauryl α-cyanoacrylate.

10. The material of claim 7 wherein said amino acid is at least one member selected from the group consisting of monoamino-monocarboxylic acids and monoamino-dicarboxylic acids.

11. The material of claim 10, wherein said amino acid is at least one member selected from the group consisting of glycine, valine, methionine, glutamic acid and tyrosine.

12. The material of claim 11, wherein from 1 to 50 parts by weight of said solid catalyst is coated on 100 parts by weight of said substrate.

13. The material of claim 7, wherein said acid-amide compound is at least one member selected from the group consisting of acetamide, butyramide, α-chloroacetamide and benzamide.

14. The material of claim 13, wherein from 1 to 50 parts by weight of said solid catalyst is coated on 100 parts by weight of said substrate.

15. The material of claim 7, wherein the ratio of said filler to said α-cyanoacrylate is from 5 to 25 parts by weight of said filler per 100 parts by weight of said α-cyanoacrylate.

16. The material of claim 7, wherein said basic amine compound is present in a solvent.

17. The material of claim 7, wherein said basic amine compound is at least one member selected from the group, consisting of N,N-dimethyl-p-toluidine, N,N-diethyl-p-toluidine, N,N-dimethylaniline and N,N-diethylaniline.

18. A method of producing a filler for an α-cyanoacrylate dental material which comprises, mixing a silica powder with a solid catalyst, said solid catalyst being at least one member selected from the group consisting of amino acids and acid-amide compounds having a weak catalytic activity to said α-cyanoacrylate in a solvent for said solid catalyst, evaporating said solvent and drying said residue.

19. The method of claim 18, further comprising the step of pulverizing said residue to a finely divided powder.

20. A method of applying an α-cyanoacrylate dental material to a tooth comprising,
forming a thixotropic composition of an α-cyanoacrylate and a filler comprising a silica powder coated with at least one solid catalyst, said solid catalyst being at least one member selected from the group consisting of amino acids and acid-amide compounds having a weak catalytic activity to said α-cyanoacrylate;
etching the tooth surface to be sealed;
washing and drying the tooth surface;
applying said mixture to said etched tooth surface; and
adding a basic amine compound having a strong catalytic activity to said α-cyanoacrylate and a pKb value of 1 to 12 in water to cure said α-cyanoacrylate.

21. The method of claim 20, wherein said etching is carried out with phosphoric acid.

22. The method of claim 20, wherein said etching is carried out with citric acid.